US008630866B2

(12) United States Patent
Warner et al.

(10) Patent No.: US 8,630,866 B2
(45) Date of Patent: Jan. 14, 2014

(54) SYSTEM AND METHOD TO AUTOMATE SERVICE DELIVERY TO MEDICAL EQUIPMENT

(75) Inventors: Adrian F. Warner, Delafield, WI (US); Crispian Sievenpiper, Waukesha, WI (US); Richard Frowein, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1146 days.

(21) Appl. No.: 12/115,675

(22) Filed: May 6, 2008

(65) Prior Publication Data

US 2009/0281822 A1    Nov. 12, 2009

(51) Int. Cl.
*G06Q 50/00* (2012.01)
(52) U.S. Cl.
USPC .................. 705/2; 705/3; 600/300; 709/219
(58) Field of Classification Search
USPC ............................ 705/2–3; 600/300; 709/219
See application file for complete search history.

(56) References Cited

U.S. PATENT DOCUMENTS

| 7,127,499 | B1 * | 10/2006 | Accardi et al. | 709/219 |
| 7,716,077 | B1 * | 5/2010 | Mikurak | 705/7.12 |
| 2002/0013714 | A1 * | 1/2002 | Dubler et al. | 705/2 |
| 2006/0143044 | A1 * | 6/2006 | Conry et al. | 705/2 |

OTHER PUBLICATIONS

Hardman, W. et al.; "A Helicopter Powertrain Diagnostics and Prognostics Demonstration," Aerospace Conference Proceedings, 2000 IEEE, vol. 6, pp. 355-365.

* cited by examiner

*Primary Examiner* — Sind Phongsvirajati
(74) *Attorney, Agent, or Firm* — Fletcher Yoder, P.C.

(57) ABSTRACT

A system and method to manage service delivery to a customer is provided. In one embodiment, a system may include a computing device that, in turn, includes a memory having a plurality of routines stored therein and a processor configured to execute the plurality of routines. The plurality of routines of one embodiment may include a response engine configured to receive an indication of an event with respect to a medical resource and to receive a plurality of region-specific parameter sets including a parameter set associated with a geographic region in which the medical resource is located. Additionally, the response engine may be configured to generate an output including a recommended action based at least in part on the event and the parameter set associated with the geographic region such that the recommended action is customized for the geographic region in which the medical resource is located.

18 Claims, 3 Drawing Sheets

SYSTEM AND METHOD TO AUTOMATE SERVICE DELIVERY TO MEDICAL EQUIPMENT

BACKGROUND

The invention relates generally to the field of service delivery and, more specifically, to a system and method to manage service delivery.

In a variety of industrial, commercial, medical, and research contexts, various pieces of equipment may be employed on a day-to-day basis to accomplish or facilitate the work being performed at a facility. In many instances, the facility may rely upon a third party to service some or all of the equipment at the site to ensure that the equipment remains operational and available. For example, in an industrial setting, production equipment or computer resources that are in operation in a continuous or near-continuous manner may be serviced by an off-site party that provides servicing as needed or requested. Similarly, hospitals, clinics, and research facilities may utilize another party to service some or all of the diagnostic, monitoring, and/or imaging equipment at a site so that the equipment remains available where and when it is needed.

BRIEF DESCRIPTION

There is a need for a system and method to managing service delivery that accounts for variables in an efficient and cost-effective manner, the variables including but not limited to: a location of the system, an availability and transit time of any necessary replacement parts for the system, an availability of personnel to perform such servicing, and to accommodate different expectations with respect to service delivery based on, for example, cost considerations, local considerations, or the like. The subject matter described herein is operable to address the needs and concerns described above. Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

According to one embodiment, a system is provided. The system may include a computing device, which may include a memory having a plurality of routines stored therein and a processor configured to execute the plurality of routines. In one embodiment, the plurality of routines includes a response engine that may be configured to receive an indication of an event with respect to a medical resource and to receive a plurality of region-specific parameter sets including a parameter set associated with a geographic region in which the medical resource is located. The response engine may also be configured to generate an output including a recommended action based at least in part on the event and the parameter set associated with the geographic region such that the recommended action is customized for the geographic region in which the medical resource is located.

According to another embodiment, a method is provided. The method includes a step of receiving a signal indicative of an event for a medical system located in a particular geographic region of a plurality of geographic regions. Further, the method may include a step of generating, via a computer, a recommended service action in response to the signal, wherein generating the recommended service action may be based at least in part on a set of parameters including at least one of a parameterized operational requirement or a parameterized commercial requirement. Also, in one embodiment, the set of parameters may be customized for the particular geographic region in which the medical system is located such that the generation of the recommended service action accounts for variance of at least one of operational requirements or commercial requirements between the different geographic regions of the plurality of geographic regions. This method may also include a step of generating an output illustrative of the recommended service action.

According to yet another embodiment, a manufacture including a computer-readable medium is disclosed. Executable instructions may be stored on the computer-readable medium, and may include, in one embodiment, instructions to receive a signal indicative of an event for a medical system located in a particular geographic region of a plurality of geographic regions. The executable instructions may also include instructions to generate a recommended service action in response to the signal, wherein generating the recommended service action may be based at least in part on a set of parameters including at least one of a parameterized operational requirement or a parameterized commercial requirement. Still further, in one embodiment, the set of parameters may be customized for the particular geographic region in which the medical system is located such that the generation of the recommended service action accounts for a variance of at least one of operational requirements or commercial requirements between the different geographic regions of the plurality of geographic regions. Additionally, the executable instructions may also include instructions adapted to output the recommended service action.

Various refinements of the features noted above may exist in relation to various aspects of the subject matter described herein. Further features may also be incorporated in these various aspects as well. These refinements and additional features may exist individually or in any combination. For instance, various features discussed below in relation to one or more of the illustrated embodiments may be incorporated into any of the above-described aspects of the subject matter of the application alone or in any combination. Again, the brief summary presented above is intended only to familiarize the reader with certain aspects and contexts of the subject matter herein without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Certain embodiments of the present invention may generally relate to a system and a method for managing service delivery to a client. In some embodiments, a method includes routing automated triggers or alarms indicative of a present or future service need with respect to a given system or component into a response engine, which may be configured to determine an optimal service action in response to the trigger or alarm. Such a determination may be made in view of various parameters, including, for example, one or more of the type of system event initiating a trigger or other service request, region-specific parameters, and customer-specific parameters. In various embodiments, region-specific parameters can include replacement part delivery times, response time targets, personnel available to perform servicing, expected repair time, or the like. Customer-specific parameters may include, among other things, cost considerations and contractual obligations between the customer and the service provider. Consequently, in various embodiments, the presently disclosed system and method may facilitate service delivery in a more flexible and efficient manner.

Figure 1:
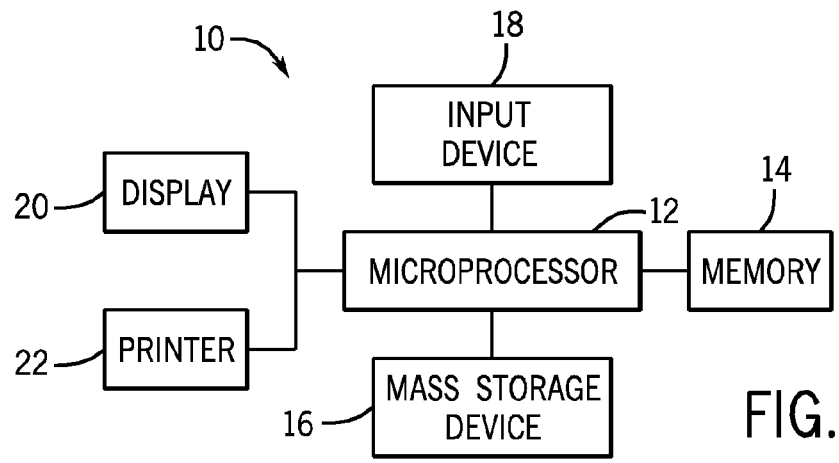
FIG. 1 is a block diagram illustrative of an embodiment of a processor-based device or system of the subject matter described herein.

Referring first to FIG. 1, an embodiment of a processor-based system 10 for use in conjunction with the present technique is depicted. The processor-based system 10 can be a general-purpose computer, such as a personal computer, configured to run a variety of software, including software implementing all or part of the present technique. Alternatively, in other embodiments, the processor-based system 10 may comprise, among other things, a mainframe computer, a distributed computing system, or an application-specific computer or workstation configured to implement all or part of the present technique based on specialized software and/or hardware provided as part of the system. Further, the processor-based system 10 may include either a single processor or a plurality of processors to facilitate implementation of the presently disclosed functionality.

In general, the embodiment of processor-based system 10 can include a microcontroller or microprocessor 12, such as a central processing unit (CPU), which executes various routines and processing functions of the system 10. For example, the microprocessor 12 may execute various operating system instructions as well as software routines configured to effect certain processes and stored in or provided by a manufacture including one or more computer readable-media, such as a memory 14 (e.g., a random access memory (RAM) of a personal computer) or one or more mass storage devices 16 (e.g., an internal or external hard drive, a solid-state storage device, CD-ROM, DVD, or other storage device). Various software routines or instructions for implementing the functionality described herein may be stored in a single computer-readable medium, or may be collectively stored in a plurality of computer-readable media, in which a subset of such routines are stored in a first computer-readable medium while the remaining routines are stored in one or more other computer-readable media (e.g., a multi-disc software set or a distributed processing system). As such, any reference herein to a memory device or computer-readable medium having a set of routines or instructions stored thereon is intended to encompass the aforementioned embodiments, including those in which the routines or instructions are distributed across multiple devices or media. In addition, the microprocessor 12 processes data provided as inputs for various routines or software programs, such as data provided as part of the subject matter described herein in computer-based implementations.

Such data may be stored in, or provided by, the memory 14 or mass storage device 16. Alternatively, such data may be provided to the microprocessor 12 via one or more input devices 18. The input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network, such as a local area network or the Internet. Through such a network device, the system 10 may exchange data and communicate with other networked electronic systems, whether proximate to or remote from the system 10.

Results generated by the microprocessor 12, such as the results obtained by processing data in accordance with one or more stored routines, may be provided to an operator via one or more output devices, such as a display 20 and/or a printer 22. Based on the displayed or printed output, an operator may request additional or alternative processing or provide additional or alternative data, such as via the input device 18. Communication between the various components of the processor-based system 10 may typically be accomplished via a chipset and one or more busses or interconnects which electrically connect the components of the system 10.

The embodiment of the processor-based system 10, or some other processor-based system, may be configured to facilitate service delivery with respect to various devices, systems, or clients. More particularly, in certain embodiments, an automated system can receive data pertaining to systems located within various regions, and can use region-specific rules, policies, constraints, and the like to automatically determine a preferred service action with respect to a triggering event in any given system.

Figure 2:
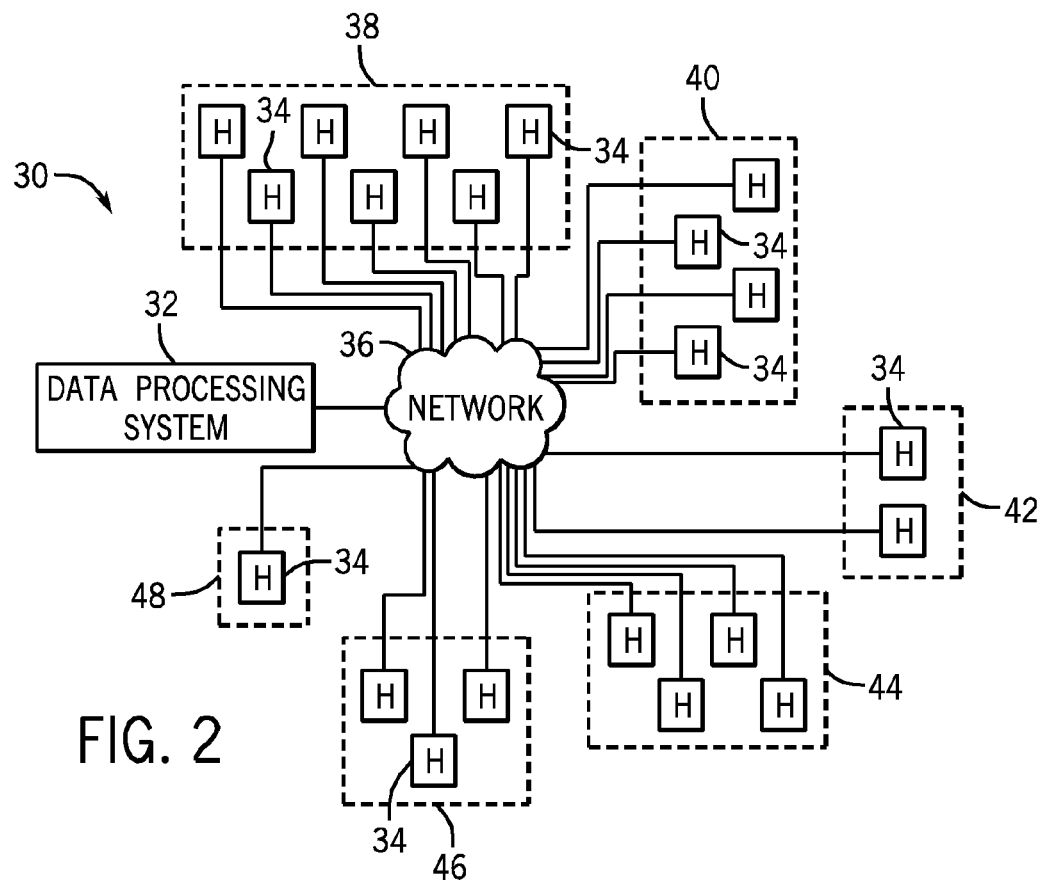
FIG. 2 is a block diagram of an embodiment of a networked system.

Referring to FIG. 2, an embodiment of a system 30 includes a data processing system 32 that can be configured to receive data from a plurality of healthcare facilities or entities 34. The data processing system 32 may include the processor-based system 10 discussed above, or may include any other devices or components. In one embodiment, the data processing system 32 can be configured to receive data from the healthcare facilities 34 via a network 36. The network 36 may include a variety of components that facilitate communication between devices, such as switches, routers, servers or other computers, network adapters, communications cables, and the like, and may include one or more local area networks, wide area networks, and so forth. For instance, in one embodiment, the network 36 may include the Internet. Data from the healthcare facilities 34 to the data processing system 32 may be automatically transmitted via the network 36. The transfer may be manually initiated at the data processing system 32 or a healthcare facility 34 and the data then transmitted via the network 36, or the data could be communicated independent of the network 36, such as through manual entry of such data into the data processing system 32.

The embodiments of the healthcare facilities 34 may include, among other things, hospitals, clinics, doctors' offices, laboratories, or the like. Further, such healthcare facilities 34 may be located in geographically distinct regions, as generally indicated by the grouping of the healthcare facilities 34 into separate regions 38, 40, 42, 44, 46, and 48. In various embodiments, such regions could correspond to different districts of a city or region, different cities in a region, different regions within a state, different states, different geographic regions of a country, different counties, different global regions, some combination of the above, or any other desired grouping. While such groupings may be defined by geographic regions in the presently illustrated embodiment, in other embodiments the various healthcare facilities 34 could be segmented or grouped based on other, non-geographic, considerations, such as patient volume.

The embodiment of the data processing system 32 facilitates management of service delivery to the healthcare facilities 34 based on rules, policies, or constraints specific to segmented groups to which the healthcare facilities 34 belong. Again, a given healthcare facility 34 can be associated with a particular segmented group on one or more of various bases, including the region in which the healthcare facility 34 is located, patient volume of the healthcare facility 34, the relative importance of a healthcare facility 34, or the like. The number of groups or regions, as well as the number of healthcare facilities 34 within each group or region, may be greatly varied. The system and method described herein may be broadly applicable to a number of industries or areas outside the field of healthcare.

Figure 3:
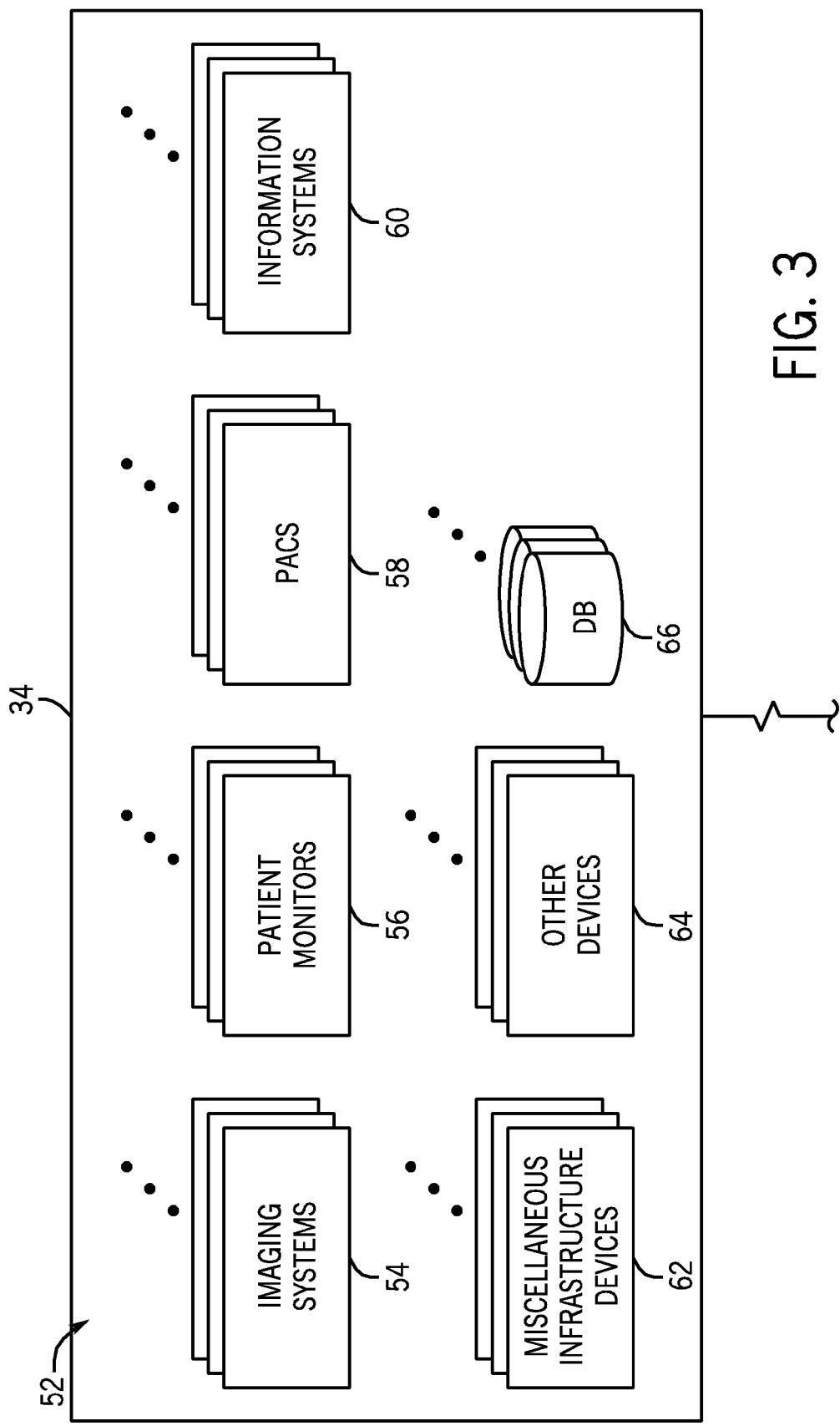
FIG. 3 is a block diagram illustrative of an embodiment of devices and systems of a healthcare facility that may be covered by a service arrangement in accordance with the subject matter described herein.

The healthcare facility 34 may employ a wide variety of devices or medical resources 52 that facilitate the provision of healthcare to its patients. Referring to FIG. 3, the example of the healthcare facility 34 may include one or imaging systems 54, such as a magnetic resonance imaging (MRI) system, a computed tomography (CT) system, an x-ray system, a positron emission tomography (PET) system, a digital tomosynthesis system, an ultrasound system, or the like. The healthcare facility 34 may also include patient monitors 56; picture archiving and communication systems (PACS) 58; information systems 60, such as a radiological information system (RIS); and miscellaneous infrastructure devices 62, such as computer workstations, servers, communication devices, and the like. Still further, the healthcare facility 34 may also include various other devices 64 and databases 66.

Various automated alarms, computer-generated events, and detection algorithms may be used in the provision of automated service with respect to a distributed device or system base. Further, triggering events with respect to a system may generally be considered as falling within one of several categories: reactive events, such as a current failure mode, that may require immediate or urgent attention; proactive events that are based on a given schedule or system condition, rather than a current failure mode; and pre-emptive events that may indicate that failure is likely to occur in the near future.

It is noted that triggering events in each of these categories may have different requirements in terms of actual service delivery, and may be perceived differently by a customer. With respect to a pre-emptive event for a given client system, such as a medical resource 52, in which failure has not yet occurred, for instance, it may be difficult to convince a customer or other end-user that the system would benefit from servicing. Further, with reactive events, race conditions may exist within the service delivery model such that the customer may contact the service provider with a service request before, or soon after, the event is detected, resulting in multiple service requests (e.g., one request generated upon automatic detection of a failure mode, and another manually generated upon notification by the customer). It may also be desirable to detect proactive events that are not being serviced, or that may become critical at some future time. Delaying action in response to event triggers for a "hold-off" period can become increasingly complex, and may increase a likelihood of regional variances in service delivery capacities and conditions.

Figure 4:
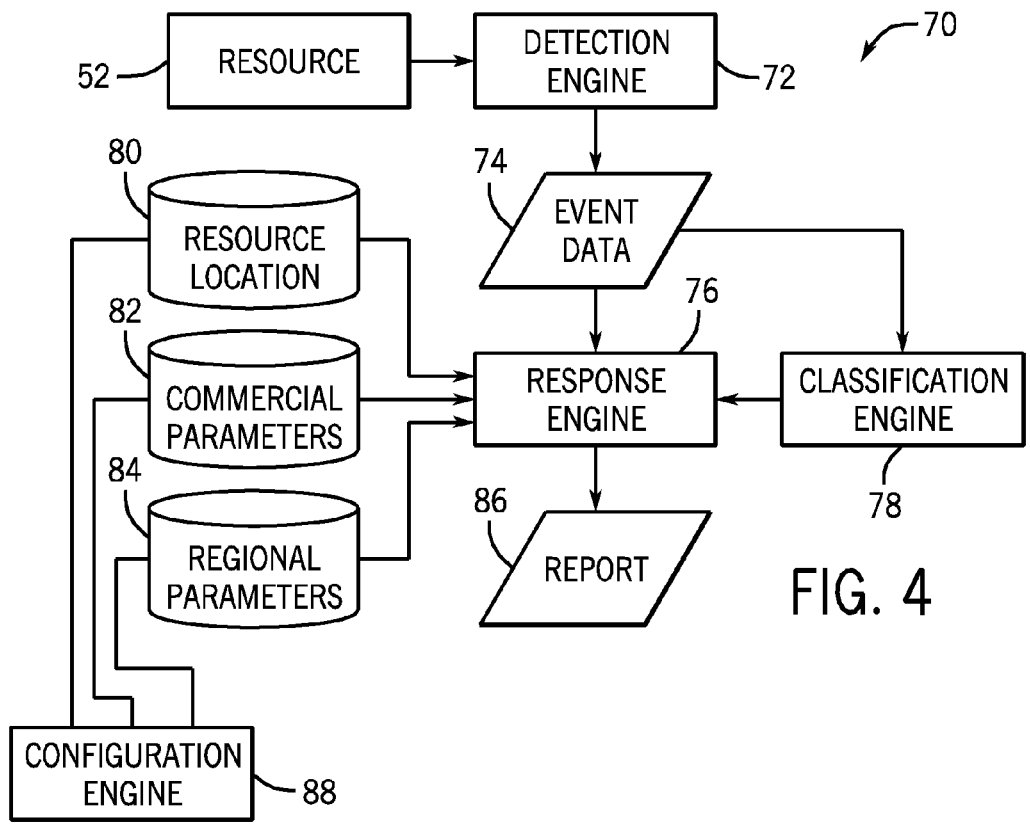
FIG. 4 is a block diagram illustrative of an embodiment of a service delivery system in accordance with the subject matter described herein.

FIG. 4 illustrates a block diagram 70 illustrative of one or more of the data processing system 32, the resources 52, or other devices, programmed with various routines to facilitate service delivery. An embodiment of a detection engine 72 can detect a triggering event with respect to the resource 52. The detection engine 72 may include any combination of hardware or software, such as a plurality of software routines and hardware that facilitates execution of such routines to perform the functionality described herein. Moreover, the detection engine 72 may be local to, or a part of, the monitored resource 52, or remote from the resource 52, such as part of the data processing system 32. The detection engine 72 may be adapted to analyze operational or other data of the resource 52 to detect various triggering or detection events, such as a malfunction of the resource 52, a prediction of a future malfunction, a time for scheduled maintenance, or the like, and may employ various automated alarms or detection algorithms.

Additionally, the detection engine 72 may output an indication of the event or other event data 74 for further analysis by a response engine 76. An embodiment of the response engine 76 may be a logic engine configured to receive the event data 74 (e.g., an indication that a triggering event has occurred with respect to a system or component) and to process such information in view of various parameters (e.g., fixed or variable parameters), constraints, policies, models, and the like to generate an optimal service action recommendation with respect to the triggering event. It should be noted that the response provided by the response engine 76 may vary depending on the classification of the triggering event (e.g., current failure, imminent failure, scheduled maintenance indication, and so forth), which may be provided via a classification engine 78. The response engine 76 may also consider other parameters, which may be stored in one or more of the databases 80, 82, or 84, or in some other location, in determining an optimal service delivery response to the triggering event. Although the databases 80, 82, and 84 are separately illustrated in FIG. 4, the parameters may be stored in a common database or other databases, and stored in one or more suitable memory devices. Such parameters may, among other things, represent system operational requirements or commercial requirements. In some embodiments, such parameters may include the location of the resource 52, such as the region in which the resource 52 is located.

Additionally, the response engine 76 may integrate or consider various commercial parameters, such as regional service cost structures or the contracted service level of a customer. For instance, a service provider may contract with different customers at various service levels, such as a "standard" service level, a "silver" service level, and a "gold" service level, in which the service provider and the customer agree to various aspects of the service arrangement including, for example, types of servicing covered by the contract, service delivery speeds with respect to covered service, service frequency, or the like. Thus, a recommended service action with respect to a triggering event of the resource 52 may depend in part on the level of contracted service.

By way of example, in the case of a given event, a triggering event may not be contractually covered under the "standard" service level, but be covered under both the "silver" and "gold" levels of service. In such an instance, the response engine may output different recommended service actions in a report 86, based at least in part on the contracted service level, as stored in the database 82. More particularly, if the customer or resource 52 is covered at the "standard" service level and the triggering event of the resource 52 is not covered under that plan, the response engine 76 may output a recommendation to the service provider to withhold service with respect to the event. If, however, the resource 52 is covered at a "silver" service level, the response engine 76 may recommend a service action to the service provider and, based on other parameters, may also recommend the timing of such service delivery. In turn, if the resource 52 is covered by the "gold" service level, the response engine 76 may recommend an accelerated service action, or may recommend for service to be performed in a manner that is different (e.g., quicker) than that which would be provided to a similar resource covered only at the "silver" service level. Additionally, the response engine 76 may, in some cases, conditionally recommend servicing of the resource 52 based on its location or based on other parameters. Further yet, if the resource 52 is unlikely to complete a given operation (e.g., a scan of a patient by an imaging device) in view of the triggering event, the response engine 76 may recommend that the resource 52 be removed from service until a service action may be performed on the resource 52.

Still further, regional parameters may be considered by the response engine 76 to allow for regional optimization of the response engine 76. For instance, regional parameters may include information specific to a given region or locality, such as estimated delivery times for replacement parts within the region, an estimated repair time for servicing within the region (which may, in turn, be based on the availability, workload, and response time of service personnel), a desired response time target within the region, and service delivery options, to name but a few. For example, the delivery time for a replacement part, such as an x-ray tube, may depend on a service provider's supply chain with respect to the replacement part. More specifically, in a scenario in which an x-ray tube is located at a warehouse in a given city, it may only take minutes or hours to the deliver the x-ray tube to another location within the city, while it may take a day to deliver the x-ray tube to another metropolitan area, and even longer to deliver such an x-ray tube from the warehouse to a distant, isolated, rural area. Additionally, customers in different regions may have different expectations with respect to response time and/or repair time.

In some embodiments, the response engine 76 can be configured to consider numerous regionally-varying parameters, including those discussed above, to determine an optimal service event recommendation with respect to a triggering event for a device or component within a given region. According to one embodiment, a configuration engine 88 may be provided to facilitate local control of the various parameters considered by the response engine with respect to a given region, allowing regional variation of response engine operation based on regional considerations and parameters. For example, the user (e.g., a service manager for a given region) may remotely access and modify parameters for the given region considered by the response engine, allowing for distributed control and locally-tailored solutions based on regional considerations and desires. Of course, such parameters for a given region may also be updated by a user not located within the region.

Figure 5:
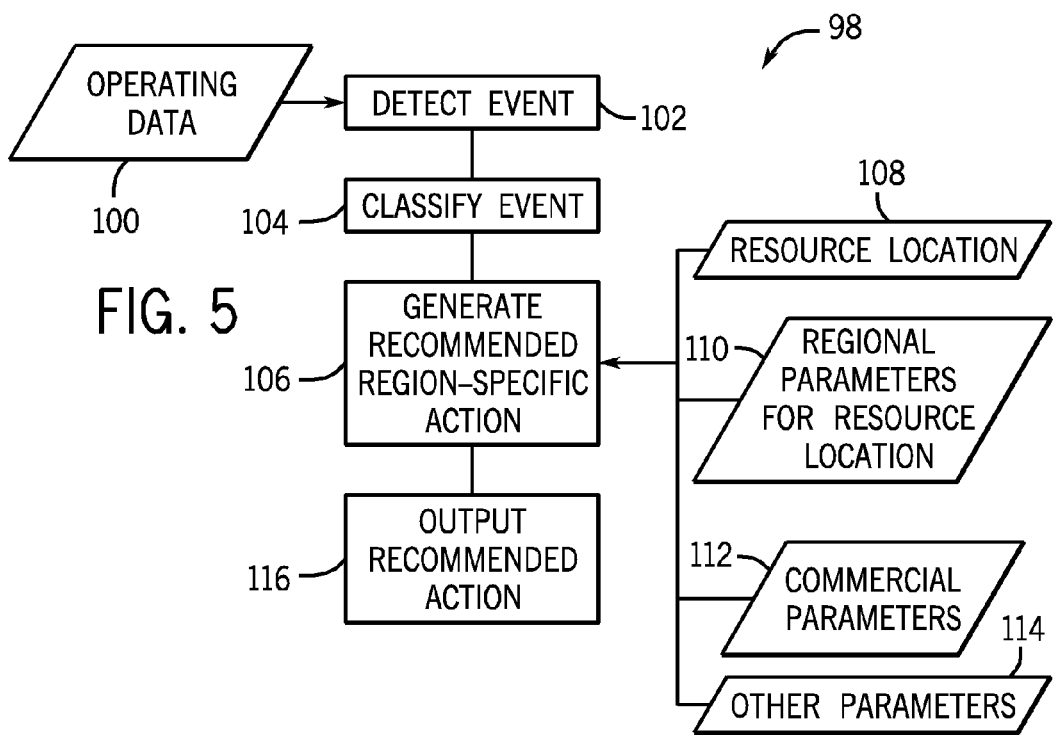
FIG. 5 is a flow diagram illustrative of an embodiment of a method to manage service delivery in accordance with the subject matter described herein.

Referring to FIG. 5, an embodiment of one or more components of the system 30, such as the data processing system 32 or a resource 52, may be configured to perform one or more steps of an exemplary method 98. Again, the steps of the exemplary method 98 may be performed as part of a software-based application stored in and executed by various hardware components, or may be performed via application-specific hardware or circuitry configured to perform such steps. The method 98 includes a step 102 of detecting a triggering event from operating data or other data 100 related to a given device or component. The method 98 may also include a step 104 of classifying the triggering event and a step 106 of generating a recommended region-specific service action. As noted above, numerous parameters may be considered in determining the recommended service action, including a resource location parameter 108, various policies or parameters 110 for the region in which the resource is located, commercial parameters 112, and other parameters 114, as generally discussed above. Based on these parameters, the recommended service action may be output in step 116. In some embodiments, the response engine 76 may automatically interface with another system, such as a part ordering or distribution system, such that outputting the recommended service action may include automatically initiating an order for a replacement part for a resource 52 based on the recommended service action.

As noted above, various healthcare facilities 34 and resources 52 may be segmented into groups based on factors other than location (e.g., based on patient volume, facility or resource importance, or the like). Consequently, in at least some embodiments, the method 98 may include generating a recommended group-specific action instead of or in addition to generating a recommended region-specific service action. For example, in one embodiment, the method 98 may include a step of generating a recommended service action with respect to a resource 52 based at least partially on the patient volume of the healthcare facility 34 using the resource 52. Of course, in other embodiments, the recommended service action may be generated based on both regional considerations as well as other group considerations.

A technical effect of the system and method described herein may include, among others, facilitating optimization of service delivery, allowing a high degree of customization with respect to service delivery based on local or regional considerations and other parameters. Some embodiments of the system and method account for variance in parameters and service delivery requirements between different groups or regions. Additionally, while certain examples are generally discussed above with respect to healthcare institutions and systems, the use of the presently disclosed system and method in other, non-healthcare related fields is also envisaged to manage service delivery with respect to other systems and components.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system comprising:
a computing device including a memory having a plurality of routines stored therein and a processor configured to execute the plurality of routines, the plurality of routines comprising:
a service response engine configured to receive an indication of an event with respect to servicing of a medical system, to classify the event by type using a classification engine, to receive a plurality of region-specific parameter sets including a parameter set associated with a particular geographic region from a plurality of geographic regions in which the medical system is located, the region-specific parameter sets including parameterized operational requirements applicable to healthcare facilities of the respective geographic regions, wherein the set of parameters is customized for the particular geographic region in which the medical system is located such that the generation of the recommended service action accounts for a variance of operational requirements for servicing of medical equipment between the different geographic regions of the plurality of geographic regions, and wherein at least one of the parameterized operational requirements is based on a target response time for servicing the medical system, and to generate an output including a recommended service action for servicing the medical system based at least in part on the type of event as determined by the classification engine and on the parameter set associated with the geographic region such that the recommended service action is customized for the geographic region in which the medical system is located.

2. The system of claim 1, the system further comprising an additional computing device configured to detect events associated with the medical system and to output the indication of the detection event.

3. The system of claim 2, the system further comprising the medical system, wherein the medical system comprises the additional computing device.

4. The system of claim 2, wherein the service response engine is configured to automatically generate the recommended service action in response to the receipt of the indication of the event.

5. The system of claim 1, wherein the service response engine is further configured to receive a plurality of group-specific parameter sets including an additional parameter set associated with a group of healthcare facilities having a common characteristic, and to generate the output including the recommended service action based at least in part on the additional parameter set.

6. The system of claim 1, wherein the parameter set associated with the geographic region includes an estimated repair time for the geographic region.

7. The system of claim 1, wherein the parameter set associated with the geographic region includes at least one customer-specific parameter.

8. The system of claim 7, wherein the at least one customer-specific parameter includes a contracted service level for a client.

9. The system of claim 1, wherein the plurality of routines stored in the memory of the computing device further includes a user-configuration engine that enables a user to access the computing device and to modify a parameter set the set of parameters specific to the particular geographic region based at least in part on regional preferences.

10. A method comprising:
receiving a signal indicative of an event for a medical system located in a particular geographic region of a plurality of geographic regions each having a plurality of healthcare facilities;
generating, via a computer, a recommended service action in response to the signal, wherein generating the recommended service action is based at least in part on a type of event that has been detected as determined by a classification engine running on the computer and on a set of parameters including at least one parameterized operational requirement applicable to healthcare facilities of the particular geographic region, wherein the set of parameters is customized for the particular geographic region in which the medical system is located such that the generation of the recommended service action accounts for variance of operational requirements for servicing of medical equipment between the different geographic regions of the plurality of geographic regions, and wherein the at least one parameterized operational requirement applicable to healthcare facilities of the particular geographic region is based on a target response time for servicing the medical system; and
generating an output illustrative of the recommended service action.

11. The method of claim 10, comprising receiving an updated set of parameters for the particular geographic region from a user located within the particular geographic region, wherein the received updated set of parameters includes a parameter applicable to healthcare facilities of the particular geographic region.

12. The method of claim 10, wherein the set of parameters is stored on a memory device of the computer prior to receiving the signal indicative of the event.

13. The method of claim 10, wherein generating the recommended service action is based at least in part on a classification of the event by the computer.

14. The method of claim 13, wherein the recommended service action includes a recommendation to replace a part of the medical system, and the set of parameters includes an estimated repair time to replace the part.

15. The method of claim 10, comprising automatically initiating an order for a replacement part for the medical system based at least in part on the recommended service action.

16. The method of claim 10, wherein the set of parameters includes at least one parameterized commercial requirement associated with a service contract between a service provider and an owner of the medical system.

17. A manufacture comprising:
a non-transitory computer-readable medium having executable instructions stored thereon that, when executed, cause a computing device to perform the executable instructions comprising:
instructions to receive a signal indicative of an event for a medical system located in a particular geographic region of a plurality of geographic regions each having a plurality of healthcare facilities;
instructions to classify the event by type;
instructions to generate a recommended service action in response to the signal, wherein generating the recommended service action is based at least in part on the type of event that has been detected as determined by the classification instructions and on a set of parameters including at least one parameterized operational requirement applicable to healthcare facilities of the particular geographic region, wherein the set of parameters is customized for the particular geographic region in which the medical system is located such that the generation of the recommended service action accounts for a variance of operational requirements for servicing of medical equipment between the different geographic regions of the plurality of geographic regions, and wherein the at least one parameterized operational requirement applicable to healthcare facilities of the particular geographic region is based on a target response time for servicing the medical system; and
instructions adapted to output the recommended service action.

18. The manufacture of claim 17, wherein the executable instructions further include instructions to facilitate remote access to a set of parameters for a given geographic region and to customize the set of parameters.

* * * * *